United States Patent [19]

Frasch

[11] Patent Number: 4,601,903

[45] Date of Patent: Jul. 22, 1986

[54] **VACCINE AGAINST *NEISSERIA MENINGITIDIS* GROUP B SEROTYPE 2 INVASIVE DISEASE**

[75] Inventor: Carl Frasch, Rockville, Md.

[73] Assignee: The United States of America as represented by the Department of Health and Human Services, Washington, D.C.

[21] Appl. No.: 729,206

[22] Filed: May 1, 1985

[51] Int. Cl.$^4$ .................... A61K 39/095; A61K 39/02
[52] U.S. Cl. .......................................... 424/92; 424/87
[58] Field of Search .................................... 424/92, 87

[56] References Cited

U.S. PATENT DOCUMENTS 3,577,527  5/1971  Edwards ............................... 424/92
4,271,147  6/1981  Helting et al. ........................ 424/92
4,451,446  5/1984  Vandevelde et al. ................. 424/92

OTHER PUBLICATIONS

Frasch, et al., Infection and Immunity, Jul. 1982, pp. 271–280, vol. 37, No. 1, "Protection Against Group B *Neisseria meningitidis* Disease: Preparation of Soluble Protein . . . ".

Wang et al., Infection and Immunity, Nov. 1984, pp. 408–414, vol. 46, No. 2, "Development of a *Neisseria meningitidis* Group B Serotype 2b Protein Vaccine and Evaluation in a . . . ".

*Primary Examiner*—Howard E. Schain
*Attorney, Agent, or Firm*—Holman & Stern

[57] ABSTRACT

The present invention discloses a vaccine against *Neisseria meningitidis* Group B, serotype 2b strain. More particularly, the present invention is related to an aluminum hydroxide adjuvanted vaccine containing only a single serotype 2 antigen being protective against both 2a and 2b meningococcal disease.

8 Claims, No Drawings

VACCINE AGAINST *NEISSERIA MENINGITIDIS* GROUP B SEROTYPE 2 INVASIVE DISEASE

BACKGROUND OF INVENTION

1. Technical Field

The present invention is directed to a vaccine against *Neisseria meningitidis* Group B, serotype 2. More particularly, the present invention is related to an aluminum hydroxide adjuvanted vaccine containing only a single serotype 2 antigen but being protective against both 2a and 2b meningococcal disease.

2. State of the Art

Although the proportion of *Neisseria meningitidis* (meningococcal) disease due to the individual serogroups varies from country to country, over 95 percent of the disease is caused by strains of group A, B, C, Y and W135. Highly effective capsular polysaccharide vaccines for serogroups A and C were developed about a decade ago (Gold, et al. Bull WHO 45:279-282, 1969-1970 and Gotschlich, et al. J. Exp. Med. 129:1349-1365. 1969. Recently, the polysaccharides for serogroups Y and W135 have been combined with those of A and C into a tetravalent vaccine (Hankins, et al. Proc. Soc. Biol. Med. 169:54-57. 1982). In contrast, group B capsular polysaccharide vaccines have proven to be essentially nonimmunogenic (Wyle, et al. J. Infect. Dis. 126:514-522. 1972 and Zolllinger, et al. J. Clin. Invest. 63:836-848. 1979) and attempts to improve the polysaccharide's immunogenicity through conjugation to protein have been unsuccessful (Jennings, et al. J. Immunol. 127:104-108. 1981) Serogroup B is presently the major cause of meningococcal disease in most temperate countries, and this combined with the lack of immunogenicity of the B polysaccharide, has necessitated development of alternative vaccines based upon the serotype proteins.

Meningococcal group B and C have been subdivided into 18 different serotypes based upon the immunological specificities of their major outer membrane proteins (Frasch, et al. Infect. Immun. 6:127-133. 1972 and Frasch, et al. J. Exp. Med. 147:629-644. 1978). The currently used procedures for meningococcal serotyping are agar gel double diffusion (Frasch, et al. Infect. Immun. 6:127-133, 1972) inhibition of solid phase radioimmunoassay and coagglutination using monoclonal antibodies adsorbed to protein A Sepharose. For reasons not yet understood only a few of these serotypes are associated with most group B and C disease. Sixty to eighty percent of the disease isolates are serotype 2 (Ashton, et al. Can. J. Microbiol. 26:1480-1488, 1980. and DeMaeyer, et al. J. Infect. 3(Suppl. 1):63-70. 1981) which has caused most B and C meningococcal epidemics (Frasch, et al. Seminars in Infectious Disease, Vol. 2. Stratton Intercontinental Medical Book Corp., NY. 304-337. 1979.)

Serotype 2 has now been subdivided into serotypes 2a, 2b and 2c based upon specific immunodeterminants present on the 41,000 dalton major outer membrane protein (Poolman, et al. J. Gen. Microbiol. 116:465-473. 1980). Serotype 2a was the major serotype associated with disease within group B until around 1980 and is still the major serotype among group C strains (Ashton, et al. Can. J. Microbiol. 29:129-136). Poolman et al, supra has documented the change from 2a to 2b in The Netherlands, and Jones and Eldridge observed that 2b has become more common in England (Abstract: Fifth International Conference on cerebrospinal meningitidis, Marseille, 1983). At present most group B serotype 2 disease is due to serotype 2b (Ashton, 1980, supra).

Serotype 2a protein vaccines have been prepared from outer membranes isolated in the form of membrane vesicles (Frasch, et al. Infect. Immun, 37:271-280. 1982). A number of these vaccines have been examined for toxicity and immunogenicity in animals (Peppler, et al. Infect. Immun. 37:264-270. 1982) and evaluated for safety and immunogenicity in adult volunteers, in whom they were found to be both safe and immunogenic (Frasch, et al). Seminars in Infectious Disease, Vol. 4., 1982; and Zollinger, et al. J. Clin. Invest. 63:836-848, 1979). The solubility characteristics of the protein vaccines were found to be important, because early vaccines which were predominantly protein became insoluble and failed to induce bactericidal antibodies in man (Frasch, et al. Seminars in Infectious Disease, Vol. 4. 1982), although found to be immunogenic in animals (Frasch, et al. J. Exp. Med. 147:629-644, 1978).

Soluble serotype 2a protein vaccines containing noncovalently bound group B meningococcal polysaccharide have been shown to induce serotype 2 specific bactericidal antibodies in several clinical studies (Frasch. Medical Microbiology, Vol. 2. Academic Press, NY. 1983). When these vaccines were evaluated in young children they were found to be less immunogenic than in adults (Frasch, et al. Med. Trop. (Marseille) 43:177-180. 1983), indicating that the use of adjuvants or the like may be required.

While serotype 2 remains the predominant cause of group B *Neisseria meningitidis* invasive disease in many parts of the world, most of this disease is now believed due to serotype 2b rather than 2a.

SUMMARY OF INVENTION

It is, therefore, an object of the present invention to provide *Neisseria meningitidis* vaccine containing a single serotype 2b component having immunogenicity against both serotype 2a and 2b strains.

It is a further object of the present invention to prepare an aluminum hydroxide adjuvanted serotype 2b vaccine capable of producing increased antibody response against both serotype 2a and 2b strains.

Other objects and advantages will become evident as the detailed description of the present invention proceeds.

DETAILED DESCRIPTION OF INVENTION

These and other objects and advantages of the present invention are achieved by a vaccine against *Neisseria meningitidis* disease, said vaccine containing a single group B, serotype 2b meningococcal antigen capable of inducing antibody in the host receiving said antigen, the antibodies produced having reactivity against both 2a and 2b meningococcal strains. Production of the antibodies in the host is substantially increased by combining the 2b antigen with aluminum hydroxide or aluminum phosphate at the neutral pH of about 7.0. Preferred materials and methods used in the present invention are now described. All publications cited hereunder are incorporated herein by reference.

Vaccine strain.

The starting material of the present invention is a spontaneously occurring nonencapsulated mutant selected on antiserum agar plates by multiple subcultures and designated 3006 M2. The serological and chemical characteristics of the mutant were compared with the parent strain, the meningococcal group B serotype 2b(hereinafter B:2b) strain 3006, obtained from Dr. Jan Poolman, University of Amsterdam, and no apparent differences were found in either the outer membrane protein patterns or in the serological reactivity between the parent and the mutant strains except for the B polysaccharide. A deposit of the 3006 M2 mutant strain has been made in the American Type Culture Collection, Rockville, MD under Accession No. 53044.

Vaccine.

The serotype 2b outer membrane protein vaccine preparation procedure was based upon the method described by Frasch, et al for serotype 2a (Frasch, et al., Infect. Immun. 37:271-280, 1982) with minor modifications. To the concentrated culture supernatant obtained by ultrafiltration was added 3 volumes of 95% ethanol. The resulting precipitate was dissolved in water then adjusted to 30 mM tris(hydroxymethyl)aminomethane, 2 mM sodium ethylenediaminetetraacetate, pH 8.5, and 5% Brij-96 (Polyoxyethylene oleyl ether, Sigma Chemical Co., St. Louis, MO). The ammonium sulfate precipitation step as described in Frasch, et al supra, was omitted due to poor solubility of the precipitated material.

After the outer membrane vesicle (OMV) preparation was treated with Brij-96 to selectively solubilize the lipopolysaccharide (LPS) and ultracentrifuged, the lipopolysachharide depleted OMV was redissolved in water rather than 5% sodium deoxycholate for sterile filtration. The protein was next ethanol precipitated and washed with ethanol to remove residual detergent. The protein concentration was determined on a test sample and based upon this, an appropriate amount of 3% (wt/vol) lactose was prepared in distilled water. High molecular weight group B or C polysaccharide (provided by Connaught Laboratories, Inc., Swiftwater, PA) was added to the lactose solution to a concentration of 250-1200 μg/ml polysaccharide. The polysaccharide-lactose and lactose solutions were used to prepare vaccine at 250-1200 μg/ml protein (see Table 1) and 1.0 ml was added per vial for lyophilization. The dried vaccines were reconstituted with 5.0 ml/vial of normal, sterile saline. These vaccines were compared with the previously known serotype 2A vaccines. Each vaccine were analyzed for protein by the Lowry method (Lowry, et al. J. Biol. Chem. 192:265-275. 1951) and for ketodeoxyoctonate (KDO) by the method of Osborne (Osborn, et al. Proc. Nat'l. Acad. Sci. USA 50:499-506. 1963).

A trichloroacetic acid precipitation procedure was used to separate the outer membrane vesicle material from the polysaccharide and lactose to determine protein and KDO on final container material (Bensadoun, et al. Anal Biochem. 70:241-250. 1976). Outer membrane protein patterns were determined by Tris-glycine sodium dodecyl-polyacrylamide gel electrophoresis (SDS-PAGE) as described by Tsai and Frasch, J. Bacterial. 141:169-176. 1980.

It is noted that what is obtained by the procedure described supra is a single OMV antigen but the single OMV antigen may comprise a single or a plurality of outer membrane proteins.

Adjuvants.

Aluminum phosphate and aluminum hydroxide were prepared following standard procedures well known in the art using aluminum chloride as starting material and were sterilized by autoclaving. The adjuvant preparations contained 6 mg of aluminum phospate or 1.32 mg Al/ml and 8 mg of aluminum hydroxide or 2.77 mg Al/ml, respectively. The adjuvants were diluted using saline or phosphate buffered saline (PBS), pH 7.4, the final pH being 6.0 and 7.0, respectively, and adjuvant concentration was adjusted to 1 mg/ml. Different concentrations and proportions of adjuvant to protein were used to arrive at the optimal combination as determined by ELISA and bactericidal antibodies, vide infra.

Mouse immunization and bacteremia model.

For most of the antibody studies, female NIH general purpose mice weighing 12–14 g (3 weeks old) were immunized subcutaneously (sc) or intraperitoneally (ip) with 1 μg of vaccine protein. Control mice received 10 μg of meningococcal group B or group C polysaccharide. Blood was obtained 3 to 8 weeks after immunization by cutting the right subclavian artery. The mouse bacteremia model was used as described by Craven, et al. (Infect. Immun. 26:110-117. 1979) to evaluate the level of protection induced by serotype 2b protein group B polysaccharide vaccines. For mouse bacteremia studies the mice received a single 10 μg sc injection of vaccine. Three to four weeks after immunization, animals were challenged ip with $3 \times 10^3$ CFU of the serotype 2b 3006 parent strain or the serotype 2a strain 5946.

ELISA.

The Enyzme-Linked-Immunosorbent Assay (ELISA) was performed as described by Peppler and Frasch. (Infect. Immun. 37:264–270. 1982). The OMV from serotypes 2a (M986 NCV-1) and 2b (3006 M2) were used at 2 μg/ml to coat 96 well polystyrene plates. The absorbance observed at 405 nm was extrapolated to 100 mins. and the results expressed as ELISA units.

Bactericidal Assay.

The microbactericidal assay of Frasch and Robbins. (J. Exp. Med. 147:629-644. 1978), employing serum from 4-week old rabbits diluted 1:2 as a source of complement was used to compare bactericidal antibody levels inducted by different 2b vaccines with and without adjuvant. The endpoint was defined as the highest serum dilution causing greater than 50% reduction in viable count of strain B16B6 (B:2a) or the 3006 parent strain (B:2b).

Statistical analysis.

The grometric mean ELISA values and bactericidal titers were calculated with a one standard deviation confidence interval given. Statistical significance was determined using the two-tailed Students t-test on the mean and standard deviation of log transformed data.

Analysis of serotype 2b vaccines used for immunogenicity and production studies.

The mutant 3006 M2 had an outer membrane profile on SDS-PAGE indistinguishable from that of the parent strain, which is very similar to that of the 2a pattern previously reported (Frasch, et al. Infect. Immun. 37:271-280). 1982). The vaccine lots used in these studies are show in Table 1. The chemical composition was determined on final container material. The polysaccharide content shown is based upon the dry weight added to the lactose solution. All vaccines had low amounts of lipopolysaccharide. The protein pattern of the vaccines on SDS-PAGE was the same as the 2a vaccines reported previously. (Frasch, et al. supra)

Effect of group B and C meningococcal polysaccharides on immunogenicity of the protein.

Previous results obtained using serotype 2a vaccines indicated that addition of group B meningococcal polysaccharide improved the solubility and immunogenicity of the protein. The group B polysaccharide alone is nonimmunogenic in mice. The group C meningococcal polysaccharide, although poorly immunogenic alone, is quite immunogenic when noncovalently combined with meningococcal outer membrane protein (Beuvery, et al. Infect. Immun. 40:369-380. 1983). It, therefore, needed to be determined whether the immunogenicity of the protein could be further improved by the use of an immunogenic polysaccharide carrier (Table 2). Although both polysaccharides improved the anti-protein response, no difference was found in the antibody levels to the serotype 2b protein in vaccines containing either group B or group C polysaccharide. The group B polysaccharide was therefore used for the later tests.

TABLE 1

Chemical Characteristics of the serotype 2b protein vaccines used in immunogenicity studies

| Vaccine[a] Lot | Protein (μg/vial) | Polysaccharide (μg/vial) | Lipopolysaccharide[b] (μg/mg protein) |
|---|---|---|---|
| 820622 V | 278 | — | 6.9 |
| 820622 VB | 170 | 250 | 6.9 |
| 820622 VC | 170 | 250 | 6.9 |
| 821012 VC | 182 | 250 | ND[c] |
| 830207 VM | 715 | 1,000 | <6 |
| 830207 VBM | 485 | 500 | <6 |
| 830207 VCM | 525 | 500 | <6 |
| 830207 VBH | 1,366 | 1,200 | <6 |

[a]The vaccine containing only protein was identified by the suffix V and vaccines prepared with group B or C polysaccharide were given suffixes VB and VC, respectively. Vaccines designated VBM and VBH were prepared for mouse and human studies, respectively, from the same vaccine bulk.
[b]The lipopolysaccharide content was calculated based upon a KDO content of 5%.
[c]ND, not determined.

TABLE 2

Effect of the meningococcal group B and C polysaccharides on the immunogenicity of the type 2b protein in mice

| Vaccine Lot[a] | No. of mice | GM ELISA[b] 2b | GM bactericidal titer[c] 2b |
|---|---|---|---|
| 820622 V | 6 | 0.07 (.02–.24) | 40 (25–62) |
| 820622 VB | 6 | 0.63 (.30–1.31) | 50 (28–88) |
| 820622 VC | 6 | 0.55 (.34–.92) | 56 (16–191) |
| 830207 V | 10 | 0.38 (.13–1.03) | 24 (9–56) |
| 830207 VB | 10 | 0.70 (.25–1.90) | 116 (62–221) |
| 830207 VC | 10 | 0.70 (.21–2.32) | 60 (30–135) |

[a]The vaccines were administered subcutaneously at a dose of 1.0 μg protein. The animals were bled 4 weeks later.
[b]ELISA values are equal to the absorbance at 405 nm extrapolated to 100 min for sera diluted 1/225. Geometric means and the 1 standard deviation confidence limits of the ELISA values are presented.
[c]Geometric means and the 1 standard deviation confidence limits of bactericidal titers were calculated from and expressed as the reciprocal of the highest serum dilution producing >50% killing.

Studies using adjuvants.

Aluminum adjuvants were examined for their ability to improve the immunogenicity and cross-protection of 2b vaccines. Initial tests compared mixing aluminum hydroxide with fluid vaccine and using it to reconstitute lyophilized vaccine. Both procedures yielded comparable immunogenicity. Most tests were, therefore, performed using aluminum hydroxide or aluminum phosphate as a diluent for reconstitution of lyophilized vaccine. The adjuvant properties of aluminum hydroxide and aluminum phosphate for serotype 2b protein were compared (Table 3). Preliminary experiments indicated that peak antibody responses without alum occurred at 3 and 4 weeks respectively following ip and sc immunization, but that the magnitude of the antibody response was the same. The sc route approximates the immunization route used in clinical studies and was, therefore, used for these studies. As shown in Table 3 the adjuvants gave the best results when the protein and alum were combined with the protein at the higher pH. At pH 7 both adjuvants caused significantly higher bactericidal antibody responses compared to the vaccine 830207-VB alone. The aluminum hydroxide had better adjuvant properties than aluminum phosphate for the serotype 2b protein and resulted in higher ELISA and bactericidal antibody levels that were cross-reactive with the serotype 2a protein. With adjuvant, peak antibody levels occurred 5 to 6 weeks after immunization.

TABLE 3

Comparison of the effects of different adjuvants on the antibody response of mice to serotype 2b protein vaccine

| Vaccine[a] Lot | Adjuvant[b] | pH | GM ELISA[c] 2a | GM ELISA[c] 2b | | GM Bactericidal titer[c] 2a | GM Bactericidal titer[c] 2b |
|---|---|---|---|---|---|---|---|
| 830207 V | None | ND[d] | 0.03 (.01–.17) | 0.34 (.18–.60) | ND | 24 | (9–56) |
| 830207 VB | None | ND | 0.07 (.04–.14)[e] | 0.59 (.28–1.62)[f] | ND | 116 | (62–221)[g] |
| | Al(OH)₃ | 6.0 | 0.07 (.04–.14) | 0.61 (.21–1.81) | <20 | 42 | (5–351) |
| | | 7.0 | 1.19 (.58–2.46)[e] | 0.98 (.49–1.95)[f] | 806 (285–2280) | 1381 | (1339–264) |
| | Al(PO₄) | 6.0 | 0.27 (.15–.50) | 0.35 (.25–.49) | 123 (20–756) | 348 | (127–958) |
| | | 7.0 | 0.84 (.24–2.87)[e] | 0.93 (.72–1.18)[f] | 92 (36–229) | 1194 | (377–3782) |

[a]The vaccines were administered subcutaneously at a dose of 1.0 μg into groups of 10 mice. The mice were bled 4 weeks later.
[b]Aluminum hydroxide and aluminum phosphate were used at a protein to adjuvant ratio of 1:100.
[c]See footnotes b and c of Table 2.
[d]ND, not determined.
[e]Both of the adjuvants at pH 7.0 caused significantly higher antibody responses than without, $p < 0.001$
[f]No adjuvant versus either adjuvant, $p < 0.1$
[g]No adjuvant versus either adjuvant, $p < 0.001$ The antibody response to the group B polysaccharide in mice given the 830207VB vaccine with aluminum adjuvant was tested by the polylysine precoat ELISA procedure (Leinonen and Frasch. Infect. Immun. 38:1203-1207, 1982). It was expected that the adjuvant would help induce an antibody response to the protein complexed polysaccharide, but using sera obtained 4 weeks after immunization, the polysaccharide appeared to be essentially nonimmunogenic. Less than one mouse in 20 responded with measurable B polysaccharide antibodies (IgM).

Hence, the effect of different protein (antigen) to aluminum hydroxide ratios upon the antibody response to the serotype 2a and 2b proteins were tested (Table 4). Aluminum hydroxide at pH 7.0 was combined with the protein-polysaccharide vaccine at ratios of antigen to adjuvant from 1:10 to 1:100. The 1:100 ratio was superior. Without adjuvant the degree of cross-reactivity between 2b and 2a was very low. The 2b antibody response to 1 µg of vaccine at the 1:100 ratio as measured by ELISA and bactericidal titer did not appear to be significantly different from the 20 or 50 µg doses. The effect of a booster immunization upon the serotype 2b antibody response was also tested (Table 5). Following a single booster injection, with or without adjuvant, the ELISA and bactericidal antibody levels were elevated, but less than two-fold. The second injection had a greater relative effect on the vaccine given without adjuvant.

TABLE 5-continued

Comparison of the homologous antibody response to serotype 2b vaccine lot 830207 VB with and without a booster[a]

| Protein: Adjuvant | Booster[b] | GM ELISA[c] | p value[d] | GM Bactericidal titer[c] | value[d] |
|---|---|---|---|---|---|
| | Yes | 1.12 (.83–1.52) | <0.05 | 1470 (948–2279) | <0.1 |

[a]The vaccine was administered subcutaneously at a dose of 1.0 µgG protein with and without aluminum hydroxide to groups of 10 mice. The nonboosted animals were bled at 4 wks.
[b]The booster was given 4 wks. after the primary immunization, and animals were bled 2 weeks later.
[c]See footnotes b and c of table 2.
[d]In each case, the t-test was performed on the log transferred values comparing for each set booster and no boost.

Comparison of serotype 2a and 2b vaccines.

The 2a and 2b protein-polysaccharide vaccines were given with and without aluminum hydroxide to compare the ability of the two vaccines to induce cross-reactive antibodies (Table 6). Induction of bactericidal antibodies was assumed to be an indicator of cross-protection. The 2b vaccine lot 830207VB combined with

TABLE 4

Effects of different ratios of protein to aluminum hydroxide on the antibody response of mice injected with serotype 2b protein group B polysaccharide vaccines.

| Vaccine Lot | Protein: adjuvant[a] | Dose (µg protein) | No. of mice | GM ELISA[b] 2a | GM ELISA[b] 2b | GM Bactericidal titer[b] 2b |
|---|---|---|---|---|---|---|
| 830207 VBM | 1:0 | 1.0 | 10 | 0.02 (.01–.05)[c] | 0.32 (.18–.56)[d] | 92 (39–215)[e] |
| | 1:10 | 1.0 | 10 | 0.36 (.14–.91)[c] | 1.13 (.83–1.55)[d] | 393 (139–1110) |
| | 1:20 | 1.0 | 10 | 0.30 (.13–.70) | 1.11 (.91–1.35) | 242 (57–1020) |
| | 1:40 | 1.0 | 10 | 0.54 (.35–1.21) | 1.41 (1.04–1.91) | 368 (106–1270) |
| | 1:100 | 1.0 | 10 | 0.98 (.71–1.32)[c] | 1.72 (1.48–1.99)[d] | 787 (231–2681) |
| | 1:10 | 20.0 | 5[f] | 0.73 | 1.45 | 640 |
| | | 50.0 | 5[f] | 0.88 | 1.55 | 1,280 |
| | 1:20 | 20.0 | 5[f] | 1.24 | 1.52 | 1,280 |
| | | 50.0 | 5[f] | 1.43 | 1.55 | 1,280 |

[a]The amount of adjuvant present was determined as aluminum hydroxide.
[b]See footnotes b and c of Table 2. The animals were immunized s.c. and bled 4 weeks later.
[c]The 2a immune response at the 1:100 ratio was significantly higher than either 1:0 or 1:10 at p < .001.
[d]No adjuvant versus 1:10, p < .001; adjuvant at 1:10 versus 1:100, p < .002.
[e]Adjuvant at 1:10 was significantly better than no adjuvant (p < 0.001), but not different from 1:100 (p < 0.2).
[f]The ELISA and bactericidal results were obtained on serum pools, five mice per po.

TABLE 5

Comparison of the homologous antibody response to serotype 2b vaccine lot 830207 VB with and without a booster[a]

| Protein: Adjuvant | Booster[b] | GM ELISA[c] | p value[d] | GM Bactericidal titer[c] | value[d] |
|---|---|---|---|---|---|
| 1:0 | No | 0.21 (.10–42) | | 116 (62–221) | |
| | Yes | 0.41 (.16–1.01) | <0.1 | 240 (105–556) | <0.05 |
| 1:100 | No | 0.76 (.51–112) | | 1194 (959–1407) | | aluminum hydroxide at pH 7.0 stimulated the highest bactericidal antibody levels against both serotype 2a and 2b strains. The 2a vaccines stimulated almost no bactericidal antibodies against the serotype 2b test strain, with or without adjuvants.

In order to estimate the degree of cross-immunity that could be expected from the use of a serotype 2B antigen, the 2b vaccine was evaluated in the mouse bacteremia model for ability to induce both homologous (2b) and heterologous (2a) protection (Table 7). Groups of mice were immunized with 10 µg of protein in adjuvant, and challenged 3 to 4 weeks later with a B:2a or B:2b strain. The serotype 2b vaccine induced protection against both the 2a and 2b strains. Aluminum hydroxide was the better adjuvant. In similar experiments, immunization with the group B polysaccharide alone failed to protect the mice against group B challenge.

TABLE 6

Comparison of the antibody response of mice to serotype 2a and 2b protein vaccines with and without aluminum hydroxide[a]

| Vaccine Lot | Serotype | Adjuvant Present | pH | GM ELISA[b] 2a | 2b | GM Bactericidal titer[b] 2a | 2b |
|---|---|---|---|---|---|---|---|
| 790626 VB | 2a | No | | 0.66 (.21–2.11)[c] | ND[d] | 60 (41–87) | <10 |
| | | Yes | 6.0 | 1.45 (.96–2.18)[c] | ND | 80 (49–130) | 17 (3–98) |
| 3179 VB | 2a | No | | 0.64 (.20–2.07)[c] | ND | 30 (5–172) | <10 |
| | | Yes | 6.0 | 1.65 (.95–2.87)[c] | ND | 69 (22–200) | <10 |
| 821012 VC | 2b | No | | ND | 0.71 (.33–1.54) | ND | 80 (16–396) |
| | | Yes | 6.0 | ND | 1.25 (.90–1.74) | 52 (36–77) | 242 (69–854) |
| 830207 VB | 2b | No | | 0.02 (0.01–.06) | 0.24 (.16–36)[e] | ND | 92 (54–154) |
| | | Yes | 7.0 | 0.89 (.26–3.00) | 1.13 (.84–1.52)[e] | 519 (95–2843)[f] | 1689 (453–6291)[f] |

[a]The animals received 1 μg of vaccine protein s.c. and were bled 6 weeks later. There were 5 and 10 mice per group for the 2a and 2b vaccines, respectively.
[b]See footnotes b and c of table 2.
[c]The antibody responses to 2a vaccines were not statistically different with and without adjuvant.
[d]ND, not determined.
[e]Vaccine with adjuvant versus without adjuvant, $p < 0.001$.
[f]The serotype 2a and 2b immune responses were not statistically different at $p < 0.05$.

TABLE 7

Cross protection induced by serotype 2b protein B polysaccharide vaccine lot 830207 VB in a mouse bacteremia model

| Challenge Strain | Adjuvant | Protein: Adjuvant[a] | Percent Protection[b] 3 hr. | 6 hr. |
|---|---|---|---|---|
| 3006 (B:2b) | Al(OH)$_3$ | 1:10 | 40 | 100 |
| | | 1:20 | 40 | 100 |
| | AlPO$_4$ | 1:10 | 20 | 100 |
| | | 1:20 | 20 | 100 |
| S-946 (B:2a) | Al(OH)$_3$ | 1:10 | 40 | 100 |
| | | 1:20 | 40 | 100 |
| | AlPO$_4$ | 1:10 | 40 | 80 |
| | | 1:20 | 40 | 60 |
| | Adjuvant control | | 0 | 0 |

[a]For all groups, expecting the adjuvant control, the mice received a single s.c. injection of 10 μg protein with the protein to aluminum hydroxide ratios shown.
[b]Groups of 10 mice were challenged intraperitoneally with $3 \times 10^4$ CFU of strain 3006 (B:2b) or S-946 (B:2a) 3–4 weeks after s.c. immunization. The percentage of mice without detectable bacteremia at 3 and 6 h. after challenge was calculated as percent protection.

HUMAN TESTS

The immunogenicity of the vaccine of the present invention was also tested in humans. Four groups of adults were selected for this purpose.

Group 1. received only the aluminum hydroxide adjuvant (Placebo).

Group 2. received two injections of 25 μg of vaccine reconstituted in saline (no adjuvant).

Group 3. received two injections of vaccine reconstituted in the aluminum hydroxide adjuvant.

Group 4. received the first injection of vaccine with adjuvant and the second injection with vaccine reconstituted in saline only (no adjuvant).

The results are shown in Tables 8–10.

Table 8 shows the antibody response measured by an enzyme linked immunosorbent assay (ELISA) using outer membrane material recovered from the vaccine strain containing multiple proteins and lipopolysaccharide. The data indicate that the adjuvant improved the antibody response, but that the second injection did not require adjuvant.

Table 9 shows the serotype 2b bactericidal antibody response. Most individuals lacked bactericidal antibodies in their pre-immunization sera, however, following immunization up to 90% had titers of 1:8 or greater.

TABLE 8

Serotype 2b antibody response in adults to a serotype 2b protein vaccine given without and with an aluminum hydroxide adjuvant as measured by ELISA

| Vaccine | Adjuvant 1° | 2° | n= | Geometric mean antibody response + 1 SD* Week: 0 | 3 | 6 | 10 | Significance** |
|---|---|---|---|---|---|---|---|---|
| None | — | — | 12 | 1.1 0.3–6.0 | 1.1 0.3–6.1 | 1.2 0.3–6.0 | 1.2 0.3–5.9 | N.S. |
| B830207V | No | No | 10 | 1.3 0.5–3.4 | 2.3 0.9–5.4 | 1.9 0.7–5.3 | 2.6 1.1–6.4 | $P < 0.1$ |
| | Yes | Yes | 12 | 0.8 0.4–1.9 | 2.5 1.0–6.5 | 2.0 0.9–4.5 | 3.7 1.8–7.5 | $P < 0.001$ |
| | Yes | No | 12 | 1.4 0.7–2.5 | 3.7 1.8–7.5 | 2.6 1.6–4.4 | 4.5 2.5–7.9 | $P < 0.001$ |

*25 μg of vaccine was given on weeks 0 and 6.
**Significance determined by Student's t test by comparing the antibody levels of weeks 0 and 10.

TABLE 9

Serotype 2b bactericidal antibody response of adults following immunization with a serotype 2b protein-group B polysaccharide vaccine administered with and without aluminum hydroxide adjuvant (B830207V)

| Adjuvant Present | | n= | Geometric mean bactericidal titer[A] + 1 SD | | | | Percent response[B] | Significance[C] |
|---|---|---|---|---|---|---|---|---|
| 1° | 2° | | week: 0 | 3 | 6 | 10 | | |
| No | No | 10 | 2.5 | 7.6 | 6.1 | 9.2 | 60% | p < 0.001 |
| | | | 1.4–4.7 | 3.8–15.1 | 2.9–12.8 | 4.5–18.8 | | |
| Yes | Yes | 12 | 3.0 | 9.0 | 8.5 | 17.0 | 75% | P < 0.001 |
| | | | 1.7–5.2 | 3.1–21.6 | 3.0–24.1 | 9.1–31.6 | | |
| Yes | No | 12 | 2.4 | 7.1 | 5.3 | 15.1 | 92% | P < 0.001 |
| | | | 1.7–3.2 | 2.6–19.7 | 2.4–12.0 | 7.1–32.0 | | |

[A]The bactericidal titers were determined using normal human serum as a complement source
[B]The percent responders calculated as the percent of individuals with a four-gold or greater increase in bactercidal titer
[C]The preimmunization titers (week 0) were compared to the

TABLE 10

Serotype 2a antibody response measured by ELISA in adults immunized with a serotype 2b protein vaccine administered with and without aluminum hydroxide adjuvant

| Vaccine | Adjuvant | | n= | Geometric mean antibody response + 1 SD* | | | | Significance** |
|---|---|---|---|---|---|---|---|---|
| | 1° | 2° | | week: 0 | 3 | 6 | 10 | |
| None | — | — | 11 | 0.6 | 0.6 | 0.6 | 0.6 | NS |
| | | | | 0.1–3.6 | 0.1–3.4 | 0.1–3.4 | 0.1–3.8 | |
| B830207 V | No | No | 10 | 0.9 | 1.9 | 1.7 | 2.2 | P < 0.1 |
| | | | | 0.3–2.9 | 0.6–5.7 | 0.5–6.4 | 0.7–6.4 | |
| | Yes | Yes | 12 | 0.4 | 1.3 | 1.0 | 1.8 | P < 0.001 |
| | | | | 0.2–0.9 | 0.4–4.3 | 0.4–2.8 | 0.8–3.9 | |
| | Yes | No | 11 | 0.7 | 2.2 | 1.5 | 2.9 | P < 0.001 |
| | | | | 0.3–1.5 | 0.8–5.5 | 0.6–3.6 | 1.3–6.5 | |

*25 μg of serotype 2b protein vaccine was given on weeks 0 and 6.
**Statistical significance was determined by student's t test by comparing antibody levels on weeks 0 and 10.

Table 10 demonstrates that the vaccinated individuals responded to the related serotype 2a as well, as indicated by the antibodies to 2a in the sera when examined by ELISA using serotype 2a outer membrane antigen. The results show that the 2b vaccine induced antibodies to both serotype 2a and 2b.

It is further noted that the vaccine of the present invention simulated bactericidal antibodies in both mice and humans. Protection against meningococcal disease is strongly associated with the presence of the bactericidal antibodies.

It is also pointed out that all media in which the vaccine is prepared should be sterile and free of contaminating or infectious germs or microorganisms and the like. Any physiologically acceptable media such as physiological saline or buffers well known in the art could be used.

It is understood that the examples and embodiments described herein are for illustrative purposes only and that various modifications or changes in light thereof will be suggested to persons skilled in the art and are to be included within the spirit and purview of this application and the scope of the appended claims.

I claim:

1. A vaccine comprising a single group B, serotype 2b lipopolysaccharide depleted outer membrane antigen from a *Neisseria meningitidis* group B, serotype 2b strain, said vaccine having aluminum containing adjuvant and capable of inducing in a host protective antibodies against both *Neisseria meningitidis* group B, serotype 2a and 2b invasive disease.

2. The vaccine of claim 1 wherein said antigen is obtained from a *Neisseria meningitidis* mutant having American Type Culture Collection No. 53044.

3. The vaccine of claim 1 having aluminum hydroxide or aluminum phosphate adjuvant.

4. The vaccine of claim 3 wherein the ratio of antigen to adjuvant ranges from about 1:40 to about 1:100.

5. A method of protecting a host against *Neisseria meningitidis* group B, serotype 2a and 2b invasive disease, comprising administering to said host a vaccine comprising a single group B, serotype 2b lipopolysaccharide depleted outer membrane antigen from a *Neisseria meningitidis* group B, serotype 2b strain, said vaccine having aluminum containing adjuvant and capable of inducing in a host protective antibodies against both *Neisseria meningitidis* group B, serotype 2a and 2b invasive disease.

6. The method of claim 5 wherein said antigen is obtained from a *Neisseria meningitidis* mutant having American Type Culture Collection No. 53044.

7. The method of claim 5 wherein said adjuvant is aluminum hydroxide or aluminum phosphate.

8. The method of claim 7 wherein the ratio of antigen to adjuvant is about 1:100.

* * * * *